United States Patent
Owens et al.

(10) Patent No.: US 7,148,027 B2
(45) Date of Patent: Dec. 12, 2006

(54) METHOD OF ASSESSING ANTIDEPRESSANT DRUG THERAPY VIA TRANSPORT INHIBITION OF MONOAMINE NEUROTRANSMITTERS

(75) Inventors: Michael J. Owens, Lawrenceville, GA (US); Charles B. Nemeroff, Atlanta, GA (US)

(73) Assignee: Emory University, Atlanta, GA (US)

( * ) Notice: Subject to any disclaimer, the term of this patent is extended or adjusted under 35 U.S.C. 154(b) by 492 days.

(21) Appl. No.: 10/374,288

(22) Filed: Feb. 25, 2003

(65) Prior Publication Data
US 2004/0166535 A1   Aug. 26, 2004

(51) Int. Cl.
*G01N 33/53*   (2006.01)
(52) U.S. Cl. ............ 435/7.2; 435/7.21; 435/7.23
(58) Field of Classification Search ............ None
See application file for complete search history.

(56) References Cited

U.S. PATENT DOCUMENTS

| | | | |
|---|---|---|---|
| 4,108,973 A | 8/1978 | Avenia et al. | |
| 4,259,947 A | 4/1981 | Kobrinsky | |
| 4,275,150 A | 6/1981 | Vlachakis | |
| 4,288,542 A | 9/1981 | Johnson et al. | |
| 4,375,466 A | 3/1983 | Leuschner | |
| 4,649,107 A | 3/1987 | Bowsher et al. | |
| 4,652,529 A | 3/1987 | Collins et al. | |
| 5,120,641 A | 6/1992 | Hashimoto et al. | |
| 5,188,954 A | 2/1993 | Lam et al. | |
| 5,225,323 A | 7/1993 | Lam | |
| 5,256,533 A | 10/1993 | Jones et al. | |
| 5,372,813 A | 12/1994 | Mathis, Jr. et al. | |
| 5,424,185 A | 6/1995 | Lam et al. | |
| 5,750,376 A | 5/1998 | Weiss et al. | |
| 5,830,651 A | 11/1998 | Cauley et al. | |
| 5,879,902 A | 3/1999 | Roberge et al. | |
| 6,361,957 B1 | 3/2002 | Javitt | |

FOREIGN PATENT DOCUMENTS

EP   0 435 192 A2   7/1991

OTHER PUBLICATIONS

Michelle L. Gilmor, Ph.D., Michael J. Owens, Ph.D., and Charles B. Nemeroff, M.D., Ph.D.; Inhibition of Norepinephrine Uptake in Patients With Major Depression Treated With Paroxetine; American Journal of Psychiatry; Oct. 2002; pp. 1702-1710.

Michael J. Owens, David L. Knight and Charles B. Nemeroff; Paroxetine Binding to theRat Norepinephrine Transporter In Vivo; Society of Biological Psychiatry; 2000; vol. 47 pp. 842-845.

Correspondence Paroxetine Binding to the Rat Norepinephrine Transporter In Vivo; Society of Biological Psychiatry, 2000; vol. 48 pp. 954-956.

Michael J. Owens, W. Neal Morgan, Susan J. Plott and Charles B. Nemeroff; Neurotransmitter Receptor and Transporter Binding Profile of Antidepressants and Their Metabolites[1]; The Journal of Pharmacology And Experimental Therapeutics; 1997; vol. 283 pp. 1305-1322; USA.

ML Gilmor, MJ Owens, and CB Nemeroff; Paroxetine Inhibits Norepinephrine Uptake In Patients With Depression; Poster Presentation; World Federation of Biological Psychiatry, Berlin, Jul. 1-6, 2001.

ML Gilmor, MJ Owens, and CB Nemeroff; Paroxetine Inhibits Norepinephrine Uptake In Patients With Depression; Poster Presentation; 31st Annual Meeting of the Society of Neuroscience, San Diego, CA, Nov. 10-15, 2001.

*Primary Examiner*—Janet L. Andres
*Assistant Examiner*—Steven H. Standley
(74) *Attorney, Agent, or Firm*—Alston & Bird LLP

(57) ABSTRACT

A method of measuring the individual response to antidepressant drug therapy on the transport inhibition of monoamine neurotransmitters involves in vitro monitoring of radiolabeled monoamine neurotransmitter transport into cells transfected with transport proteins similar to those on neural cells of the individual being studied. The transport occurs in unbuffered serum of the individual who is undergoing or will later undergo pharmaceutical treatment for depression or other neuropsychiatric disorders. The use of buffers is avoided so that the sensitive balance of bound/free drug within the individuals serum is not disrupted prior to or during testing.

11 Claims, 2 Drawing Sheets

METHOD OF ASSESSING ANTIDEPRESSANT DRUG THERAPY VIA TRANSPORT INHIBITION OF MONOAMINE NEUROTRANSMITTERS

FIELD OF THE INVENTION

The invention relates to a method of measuring the transport of monoamine neurotransmitters, and further of using the method to determine efficacious dosages of medications for treatment of neuropsychiatric disorders in humans.

BACKGROUND OF THE INVENTION

Neurotransmitters are small molecules that carry information across a synapse from the end of one nerve cell to the end of another nerve cell. The neurotransmitters are a diverse group of chemical compounds ranging from simple amines to amino acids to polypeptides. The mechanisms by which they elicit responses in both presynaptic and postsynaptic neurons are similarly diverse. Much research has been conducted on monoamine neurotransmitters such as serotonin, norepinephirine, and dopamine. These neurotransmitters are believed to have important effects on mood and behavior.

Dysregulations in monoamine neurotransmitter systems are currently believed to play a seminal role in the neurobiological underpinnings of certain neuropsychiatric disorders, including depression, anxiety, schizophrenia, eating disorders, Parkinson's disease and sleeping disorders. The actions of these monoamine neurotransmitters are typically terminated by transport (also know as reuptake) of the transmitter back into the cell of origin via cell surface proteins known as transporters.

Treatment of neuropsychiatric disorders often involves manipulation of neurotransmitter transport systems with pharmaceutical agents that inhibit or antagonize a particular transporter. Application of an appropriate antagonist to block uptake prolongs and enhances the action of the neurotransmitter. For example, the serotonin and norepinephrine reuptake blockers, paroxetine and desipramine, respectively, are used as antidepressants.

Determination of the amount of transporter antagonism as a function of drug dose or blood concentration is most successfully studied using in vivo techniques such as positron emission tomography (PET). However, PET is a very invasive procedure that utilizes radioactive isotopes injected into the body and requires access to nearby state of the art research facilities. Because it is undesirable and difficult to use in vivo studies, the effectiveness of new medications or of particular doses of known medications are typically determined empirically by treating human patients and trying to observe discrete measures of therapeutic effectiveness as a function of drug dosage.

The potency of individual drugs to antagonize monoamine transporters can be determined in vitro using cultured cells. In such tests, cells are cultured that contain the transporters corresponding to the neurotransmitters under study. The cells are stabilized in a buffer solution appropriate for maintaining the vitality of the cells. A radioactive form of the neurotransmitter and the proposed inhibitor are added to the buffer, and transport of the radiolabeled neurotransmitter is monitored. Transport with and without the presence of various concentrations of the proposed inhibitor are compared and an overall percentage of inhibition is determined.

Traditional in vitro methods of studying neurotransmitter transport have heretofore provided general insight into the understanding of how antidepressants inhibit neurotransmitter transporters and how potent a given agent may be, but the traditional studies are often inaccurate and based upon vague correlations between overall serum drug concentrations and the predicted transport blockage provided by the drugs in the body.

Individual variations in response to treatment with transport inhibiting antidepressant drugs is little studied and not well understood. Often, to compensate for individual responses, drugs are, as noted above, simply administered to an individual in varying combinations and dosages until the most significant reduction in symptoms are observed. Such methods of determining optimum dosages are uncertain, take long periods of time, and often result in a patient being over or under-medicated for extended lengths of time.

It is desired to provide an in vitro method of studying the effectiveness of monoamine transporter inhibitors that is patient specific and that provides data useful in determining the most effective dose of inhibitor or combination of inhibitors for treatment of a neurological disorder. Such a technique should be minimally invasive and should provide an objective guidance in the determination of optimum drug combinations and dosages.

BRIEF SUMMARY OF THE INVENTION

The invention is a method of determining the effectiveness of transport inhibiting antidepressant medication upon neurotransmitter transport proteins and the uptake of monoamine neurotransmitters by cells. The method is particularly effective for determining the effectiveness of drug treatment on an individual basis in view of the varying efficacy of antidepressant drugs among individuals within the same species. The method is effective for testing an individual subject undergoing drug treatment for a neuropsychiatric disorder, who is being treated with at least one suspected monoamine neurotransmitter transport inhibitor.

The inventors have found that buffers tend to significantly alter the equilibrium of protein-bound drug to free drug within the serum, and variation of the bound/free drug ratio negatively affects the accuracy of the test method. Therefore, in accordance with the invention, no buffer solutions are added to the serum prior to or during testing, except for de minimis amounts of buffer required as a carrier for introduction of radiolabeled neurotransmitters, as discussed below.

To implement the method, a test subject is first chosen. A cell culture is developed that has transport characteristics similar to a cell system of interest. Most typically, the cell system of interest comprises the neural cells of the subject.

A baseline serum sample is derived from blood drawn from the subject prior to administration of the drug under study. After the baseline serum sample is obtained, a controlled dosage of drug for treatment of depression or another neurological disease is administered to the subject. Serum is derived from blood samples drawn from the subject after administration of the drug. The drug-containing serum contains the amount of drug normally present within the serum of the treated subject.

The cells in culture are divided into two test cultures. The first culture, labeled the baseline culture, is used to further culture the baseline serum from the subject. The second culture, labeled the drug-containing culture, is used to further culture the actual drug-containing serum drawn from the subject. After allowing the respective cells and serum samples to come in contact with each other for a short period of time, a known amount of labeled monoamine neurotransmitter is added to the serum of each culture. The amount of cellular uptake of the labeled neurotransmitter is then measured for each culture.

The overall effectiveness of the inhibitory drug may be determined by comparing the measured uptake of labeled neurotransmitter in the baseline culture compared to that of the drug-containing culture. The percentage of transporter occupancy is calculated as the fraction of measured neurotransmitter uptake in the drug-containing sample divided by the measured neurotransmitter uptake in the baseline sample, multiplied by 100.

The invented method recognizes that transport inhibition is dependent upon the amount of free drug available for transport inhibition within the serum of any particular individual. The method also recognizes that use of buffered solutions will disturb the amount of free drug available in the serum. This property has not been recognized by previous methods of measuring transport inhibition.

Transport testing in the past has emphasized the use of buffer-washed platelet preparations, buffered serum solutions, or buffered non-serum solutions as preparation solutions or mediums for cell cultures. Heretofore, actual transport studies have been conducted in complex, buffered salt solutions. If serum has been used as a medium, buffers have always been added to the serum medium in an effort to preserve the medium.

Use of buffers to manipulate or handle drug-containing serum, before or during in vitro transport of neurotransmitters, disrupts the natural equilibrium of protein-bound drug and free drug within the serum sample, thus distorting results of any study based upon such an experiment. By using serum of the tested individual to be tested, without the addition of buffers, as the medium for in vitro transport trials, the natural balance of protein-bound drug and free drug is maintained and an accurate uptake profile for that individual may be determined.

The method of analyzing drug efficacy (amount of transporter blockade) using the unbuffered serum as a test medium has broad ranging application. For instance, effective individual treatment regimens may be designed for individual patients suffering depression. Such regimens are designed by objectively determining the effect of transport inhibition under varying drug treatments. In the past, individual responses to drug treatment were measured by measures of illness severity such as the Montgomery-Asberg Depression Rating Scale or the Hamilton Depression Rating Scale. The invented method allows much more direct and accurate in vitro determinations of antidepressant drug efficacy in individuals.

By way of example, according to one embodiment of the invented method, a human patient having symptoms of depression might have a baseline serum sample prepared and then be treated with a standard dosage of paroxetine, a serotonin transporter inhibitor. If the paroxetine is ineffective in alleviating the depression of the patient, a serum sample is obtained and transport inhibition is tested using the described method. If the assay reveals that the drug is providing significant serotonin transport inhibition (typically about 80% SERT blockade), then the treatment of this individual's depression may be deemed to be not responsive to blockade of serotonin uptake, and any unnecessary dosage increases of serotonin uptake inhibitor may be avoided. If the assay reveals that the drug is providing insufficient serotonin transport inhibition, then the source of continued depression may be the result of insufficient dosage and/or concentration of free drug available within that individual, so an increased dosage of the drug may be indicated. Moreover, this method can determine the amount of transport blockade at other transporters as well. In the example above, a patient not responding to serotonin transport inhibition may benefit by addition of a drug that also blocks norepinephrine transport.

Guidance provided by this assay avoids much of the unnecessary guesswork previously associated with determining proper medication levels for individuals suffering neurological disorders.

BRIEF DESCRIPTION OF THE DRAWINGS

Figure 1:
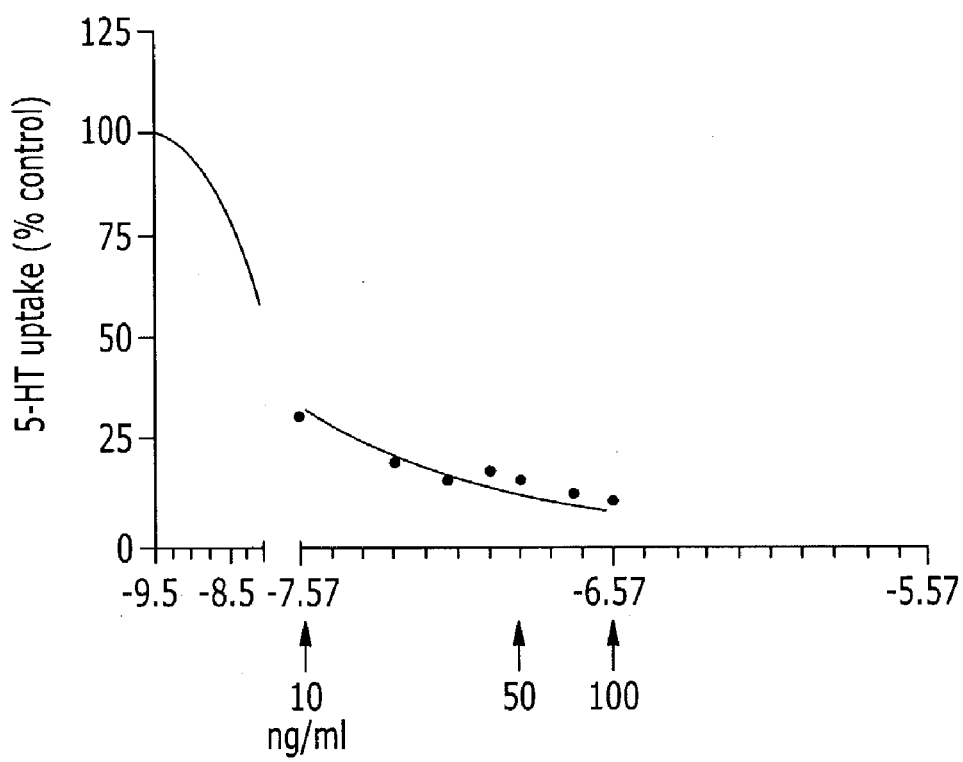
Figure 2:
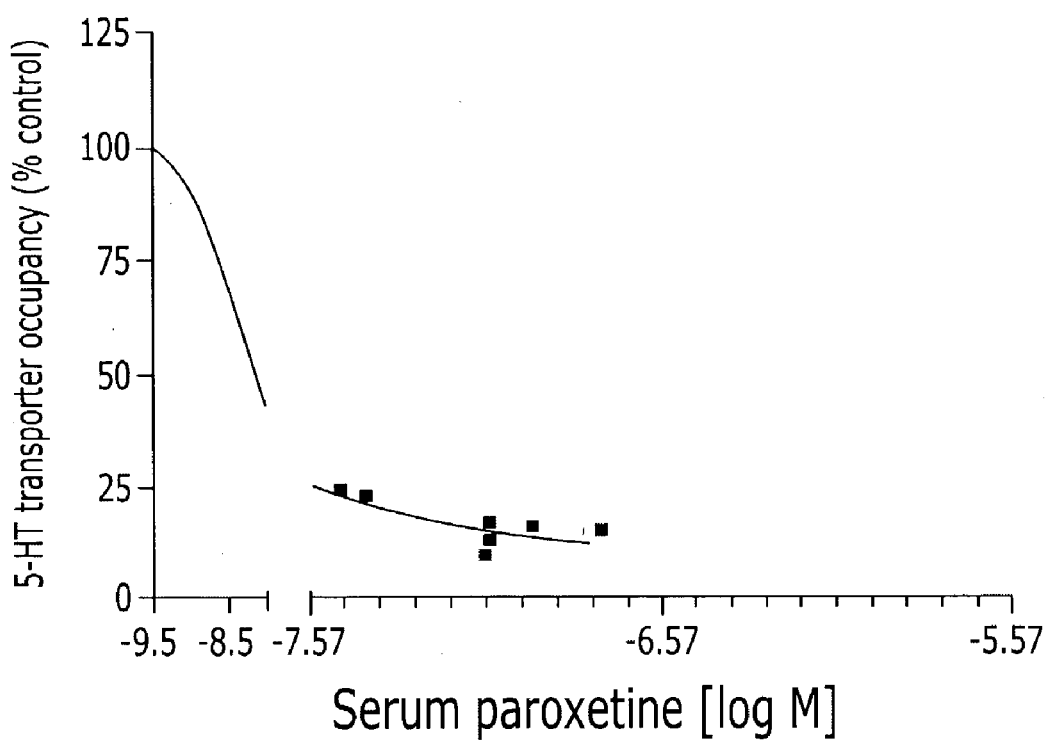
Figure 3:
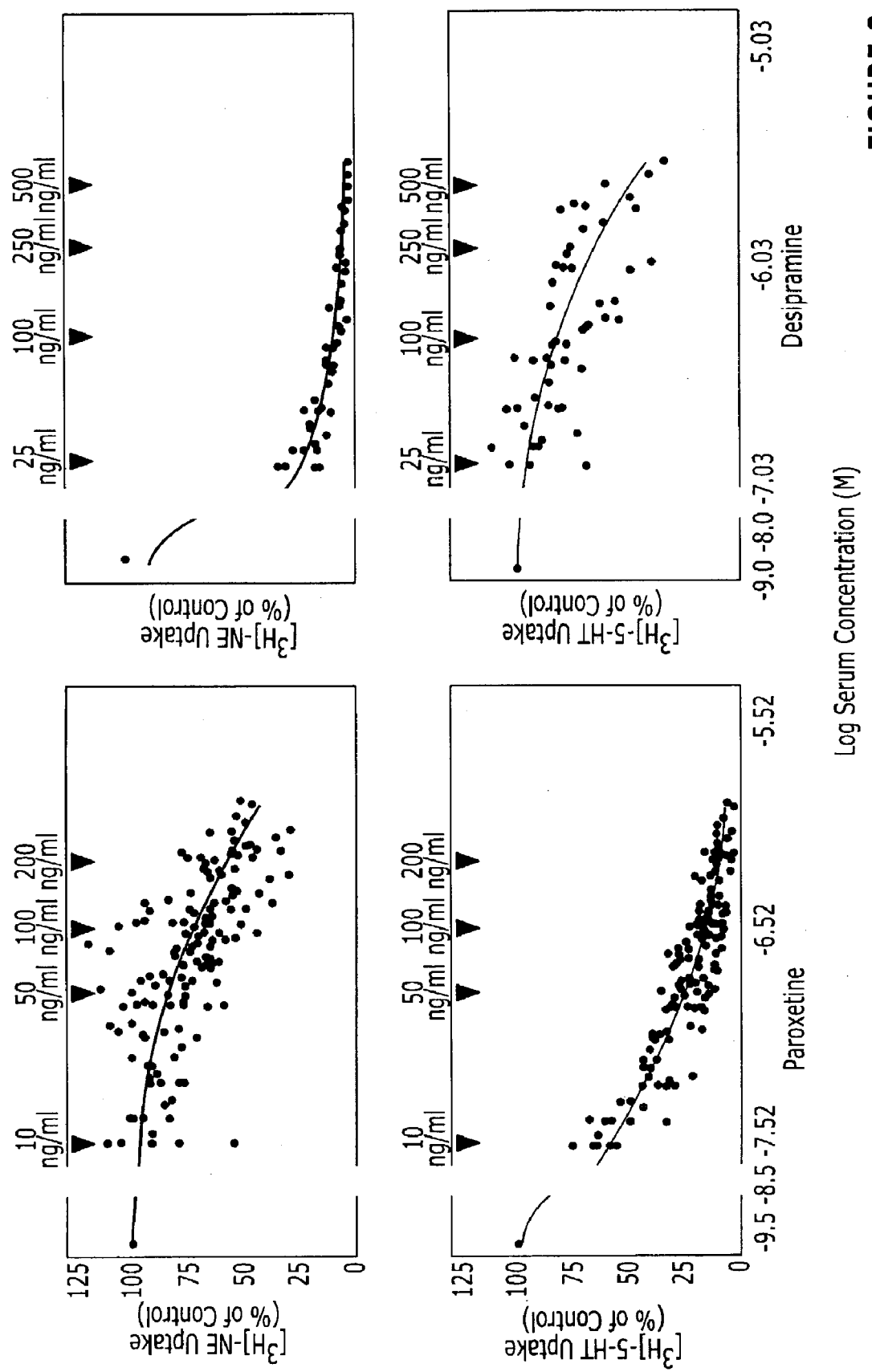

Having thus described the invention in general terms, reference will now be made to the accompanying figures, which are not necessarily drawn to scale, and wherein:

FIG. 1 is a graph showing the relationship between serotonin uptake and concentrations of serum paroxetine as measured in accordance with an embodiment of this invention;

FIG. 2 is a graph showing the relationship between serotonin uptake and concentrations of serum paroxetine as measured by PET imaging of a human brain; and FIG. 3 is a graph showing the relationship between norepinephrine and serotonin uptake and concentrations of paroxetine and desipramine in individual unbuffered human serum samples of patients receiving medication for major depressive disorder in accordance with an embodiment of the invention.

DETAILED DESCRIPTION OF THE INVENTION

The invention will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

To determine the effective monoamine neurotransmitter reuptake inhibition (transporter occupancy) of a particular subject under treatment with a particular drug dosage, a baseline measurement is determined in accordance with the techniques described below based upon serum derived from drug-free blood drawn from the subject, and drug-containing measurement is determined in accordance with the techniques described below based upon serum derived from blood drawn from the subject when the subject is undergoing drug therapy with a controlled dosage of one or more suspected antidepressant compositions. The serum samples may be freshly drawn or may be frozen and stored for subsequent testing.

For each serum sample, the serum is used as a medium for examining the transport of neurotransmitters into human transporter transfected cells. Labeled neurotransmitters are added to the serum medium and uptake of the neurotransmitters is measured. The amount of uptake varies with the amount of free drug present within the serum. The calculated transport inhibition (transporter occupancy) is determined as the quotient of the measured neurotransmitter uptake of the drug-containing sample divided by the measured neurotransmitter uptake of the drug-free sample (then multiplied by 100 to convert the fraction to a percentage).

The baseline sample is preferably derived from the subjects' own drug-free blood. However, if such a sample is not available, the test may be run using a drug-free pooled serum sample in place of the baseline sample. The drug-free pooled serum sample should have approximately the same transport inhibitory function as the drug-free serum sample of a subject.

For study of monoamine neurotransmitter transport, cell cultures are transfected with transporters selected from serotonin transporter (SERT), norepinephrine transporter (NET), or dopamine transporter (DAT). A cell culture producing a stable expression of the human SERT, NET and/or DAT, and having high-affinity, $Na^+$-dependent transport of serotonin, norepinephrine, or dopamine with pharmacological properties identical with those of native membranes can be used.

The transfected cell cultures are incubated, separately, with the baseline and drug-containing serum test media. After incubation, small, controlled amounts of radiolabeled monoamine neurotransmitters are added to the cultures. Small amounts of buffer are required at this stage in order to carry the radiolabeled neurotransmitters and to introduce the radiolabeled neurotransmitters to the test media.

The neurotransmitters, which are preferably [$^3$H]-labeled variations of serotonin, norepinephrine, or dopamine, are allowed time to be transported into the cells. The cells are then washed of excess radioactivity and overall uptake of labeled neurotransmitter is measured, and the measurements for the samples are compared to determine the transport inhibition in the drug-containing sample Little or no buffers should be added to the serum from the time the serum is drawn until the time when the cells are washed following uptake of the neurotransmitters from the serum medium, except the small amount of buffer used as a carrier for the radiolabeled neurotransmitters mentioned above. Stabilizing buffers or preservatives disrupt the ratio of free drug to protein-bound drug present in the serum, thus introducing flaws in the analysis of drug activity. As used herein, the term "buffer-free" and similar terms indicate that buffer is absent from the solution or present in such quantities that the buffer has no measurable effect on drug binding to proteins within the solution. As a practical matter, buffers preferably constitute less than about 2% by volume of the assay medium. Use of such small amounts of the buffers have no appreciable effect upon the measured transport inhibition.

This method is effective in the study of various monoamine neurotransmitters, including but not limited to serotonin, norepinephrine, and dopamine. The method is applicable to pharmaceutical compositions that inhibit the transport of monoamine neurotransmitters across cell membranes, particularly noradrenergic reuptake inhibitors, 5-HT reuptake inhibitors, dopamine reuptake inhibitors, and/or combinations thereof.

A comparison of neurotransmitter uptake in the drug treated serum with a base line sample of drug-free serum drawn from the subject provides a measurement of percent inhibition due to presence of the drug. Based upon such an outcome, overall effectiveness of the drug treatment may be examined and compared to outcomes with other drug dosages or combinations. Drug dosage or choice of drug may then be adjusted accordingly.

Whereas test conditions typically vary between test runs, for example variations in the cell culture, serum preparation, and other test conditions, it is preferred that each serum sample be tested in parallel with the baseline sample, so that the two may be compared and a percent inhibition determined. It is possible, and within the scope of this invention, however, that the test methods could be finely tuned and calibrated in order to determine a percent inhibition of a drug-containing serum sample without the need to compare the tested sample with a baseline sample.

Because unbuffered human serum is the vehicle in the assay, the free transporter-inhibiting drug in the serum samples would be expected to reflect the drug concentration in the patients' cerebrospinal fluid (CSF). In order to demonstrate the accuracy of correlation between the transporter occupancy predicted by the invented test method and actual transporter occupancy occurring in the brain of a treated subject, occupancy predicted by this method was compared to actual occupancy observed using PET imaging.

Referring to FIG. 1, pooled buffer-free human serum was spiked and equilibrated, for 2 hours at 37° C. with continuous mixing, with paroxetine. 0.3 ml of the serum was directly used for the 5-HT uptake assay in accordance with the invention. The test was repeated for several varying concentrations of paroxetine. FIG. 1 shows a graph of paroxetine concentration versus the percentage of uptake inhibition (transporter occupancy) predicted by the invented method.

Referring to FIG. 2, a graph showing serum paroxetine concentration versus actual human brain transporter occupancy was obtained from Meyer et al., 2001. American Journal of Psychiatry 158:1843-1849. The graph shows the results measured by PET imaging using PET ligand $^{[11}$C$^]$ DASB.

Comparing FIG. 1 with FIG. 2, it has been demonstrated that the transporter occupancy actually occurring within the brain (FIG. 2) is accurately reflected by the invented method (FIG. 1). Although the accuracy is demonstrated for paroxetine, it is reasonable to conclude that the transport inhibition produced by other reuptake inhibiting drugs are accurately reflected by the invented method as well.

EXAMPLES

In order to demonstrate the assay method of the invention, the method was used to determine the uptake of serotonin and norepinephrine in the presence of antidepressant drugs peroxetine and desipramine.

Background of Experiment

In an open-label, parallel-group, forced-titration study, 52 outpatients with DSM-IV major depressive disorder and a baseline Montgomery Asberg Depression Rating Scale score >20 were randomly assigned to treatment with paroxetine (to 60 mg/day) or desipramine (to 300 mg/day) in a 3-to-1 ratio, respectively. Norepinephrine and 5-HT (serotonin) transporter function were assayed by using human transporter transfected cells in the presence of serum collected at baseline and the end of each treatment week. Data from 36 patients were analyzed.

The tests were conducted in a modified monoamine uptake assay by measuring uptake inhibition of norepinephrine and 5-HT in serum samples taken from patients treated with escalating doses of paroxetine or desipramine. This method maintained the important equilibrium between free and serum-protein-bound drug, hence modeling in vivo conditions where only free drug is accessible to the brain and clinically relevant sites of action.

This was a multicenter, open-label, parallel-group, forced-titration study of paroxetine or desipramine in patients with a diagnosis of major depressive disorder. Patients were recruited by physicians at six outpatient centers. Medication assignment was determined by means of a treatment assignment sheet provided to each center such that for every four patients assigned to study treatment, three were assigned to receive paroxetine and one was assigned to receive desipramine. The 7-week dosing schedule for paroxetine was 10 mg/day for 1 week, 20 mg/day for 2 weeks, 40 mg/day for 2 weeks, and 60 mg/day for 2 weeks. The 7-week dosing schedule for desipramine was 50 mg/day for 1 week, 100 mg/day for 2 weeks, 200 mg/day for 2 weeks, and 300 mg/day for 2 weeks.

Safety and efficacy assessments were made in accordance with specifications generally accepted and approved for testing of pharmaceutical effect on neurological disorders, as further specified in Am J Psychiatry 2002; 159:1702–1710.

Analysis of Serotonin Uptake in Human Serum dosed with Paroxetine

A cell culture of HEK-293 (human embryonic kidney) cells having a stable transfection of human SERT (serotonin transporter) cDNA, and having high-affinity, Na+-dependent transport of serotonin with pharmacological properties identical with those of native membranes was provided by Dr. Randy Blakely of Vanderbilt University.

A first volume of baseline serum was derived from blood taken from the individuals at the beginning of the study. The drug-free serum was frozen and portions of the serum were thereafter unfrozen and used as needed. In each experiment, the baseline samples and all concentrations of paroxetine were assayed in triplicate in a single 24-well plate for each cell line.

Transporter uptake was assayed by aspirating the cell culture media and washing the plated cells with 0.5 ml of phosphate-buffered saline (pH=7.2) (Sigma, St. Louis, Mo.). Three hundred microliters of each serum sample was loaded into triplicate wells and preincubated for exactly 5 minutes at 37° C., after which 10 µl of [$^3$H]5-HT (40 nM final concentration; Amersham, Piscataway, N.J.) was added and the sample was incubated at 37° C. for an additional 5 minutes. The assay was terminated by aspirating the serum and washing the cells with 1.0 ml of phosphate-buffered saline. The cells were lysed with 500 µl of 0.1 M sodium hydroxide, and 450 µl was transferred to liquid scintillation vials. The [$^3$H]-5-HT uptake of the cells was quantified on a scintillation counter at 50% efficiency.

The measured [$^3$H]-5-HT uptake of each drug-containing sample was then compared to its corresponding baseline sample and the amount of uptake inhibition was calculated. The results are plotted in the lower left quadrant of FIG. 3.

Analysis of Serotonin Uptake in Human Serum dosed with Desipramine

A cell culture of HEK-293 (human embryonic kidney) cells having a stable transfection of human SERT (serotonin transporter) cDNA, and having high-affinity, Na+-dependent transport of serotonin with pharmacological properties identical with those of native membranes was provided by Dr. Randy Blakely of Vanderbilt University.

A first volume of baseline serum was derived from blood taken from the individuals at the beginning of the study. The drug-free serum was frozen and portions of the serum were thereafter unfrozen and used as needed. In each experiment, the baseline samples and all concentrations of desipramine were assayed in triplicate in a single 24-well plate for each cell line.

Transporter uptake was assayed by aspirating the cell culture media and washing the plated cells with 0.5 ml of phosphate-buffered saline (pH=7.2) (Sigma, St. Louis, Mo.). Three hundred microliters of each serum sample was loaded into triplicate wells and preincubated for exactly 5 minutes at 37° C., after which 10 µl of [$^3$H]5-HT (40 nM final concentration; Amersham, Piscataway, N.J.) was added and the sample was incubated at 37° C. for an additional 5 minutes. The assay was terminated by aspirating the serum and washing the cells with 1.0 ml of phosphate-buffered saline. The cells were lysed with 500 µl of 0.1 M sodium hydroxide, and 450 µl was transferred to liquid scintillation vials. The [$^3$H]-5-HT uptake of the cells was quantified on a scintillation counter at 50% efficiency.

The measured [$^3$H]-5-HT uptake of each drug-containing sample was then compared to its corresponding baseline sample and the amount of uptake inhibition was calculated. The results are plotted in the lower right quadrant of FIG. 3.

Analysis of Norepinephrine Uptake in Human Serum dosed with Paroxetine

A cell culture of HEK-293 (human embryonic kidney) cells having a stable transfection of human NET (norepinephrine transporter) cDNA, and having high-affinity, Na+-dependent transport of norepinephrine with pharmacological properties identical with those of native membranes was provided by Dr. Randy Blakely of Vanderbilt University.

A first volume of baseline serum was derived from blood taken from the individuals at the beginning of the study. The drug-free serum was frozen and portions of the serum were thereafter unfrozen and used as needed. In each experiment, the baseline samples and all concentrations of paroxetine were assayed in triplicate in a single 24-well plate for each cell line.

Transporter uptake was assayed by aspirating the cell culture media and washing the plated cells with 0.5 ml of phosphate-buffered saline (pH=7.2) (Sigma, St. Louis, Mo.). Three hundred microliters of each serum sample was loaded into triplicate wells and preincubated for exactly 5 minutes at 37° C., after which 10 µl of [$^3$H]norepinephrine (40 nM final concentration; Amersham, Piscataway, N.J.) were added and the sample was incubated at 37° C. for an additional 5 minutes. The assay was terminated by aspirating the serum and washing the cells with 1.0 ml of phosphate-buffered saline. The cells were lysed with 500 µl of 0.1 M sodium hydroxide, and 450 µl was transferred to liquid scintillation vials. The [$^3$H]-norepinephrine uptake of the cells was quantified on a scintillation counter at 50% efficiency.

The measured [$^3$H]-NE uptake of each drug-containing sample was then compared to its corresponding baseline sample and the amount of uptake inhibition was calculated. The results are plotted in the upper left quadrant of FIG. 3.

Analysis of Norepinephrine Uptake in Human Serum dosed with Desipramine

A cell culture of HEK-293 (human embryonic kidney) cells having a stable transfection of human NET (norepinephrine transporter) cDNA, and having high-affinity, Na+-dependent transport of norepinephrine with pharmacological properties identical with those of native membranes was provided by Dr. Randy Blakely of Vanderbilt University.

A first volume of baseline serum was derived from blood taken from the individuals at the beginning of the study. The drug-free serum was frozen and portions of the serum were thereafter unfrozen and used as needed. In each experiment, the baseline samples and all concentrations of desipramine were assayed in triplicate in a single 24-well plate for each cell line.

Transporter uptake was assayed by aspirating the cell culture media and washing the plated cells with 0.5 ml of phosphate-buffered saline (pH=7.2) (Sigma, St. Louis, Mo.).

Three hundred microliters of each serum sample was loaded into triplicate wells and preincubated for exactly 5 minutes at 37° C., after which 10 μl of [$^3$H]norepinephrine (40 nM final concentration; Amersham, Piscataway, N.J.) were added and the sample was incubated at 37° C. for an additional 5 minutes. The assay was terminated by aspirating the serum and washing the cells with 1.0 ml of phosphate-buffered saline. The cells were lysed with 500 μl of 0.1 M sodium hydroxide, and 450 μl was transferred to liquid scintillation vials. The [$^3$H]-norepinephrine uptake of the cells was quantified on a scintillation counter at 50% efficiency.

The measured [$^3$H]-NE uptake of each drug-containing sample was then compared to its corresponding baseline sample and the amount of uptake inhibition was calculated. The results are plotted in the upper left quadrant of FIG. 3.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An assay method for identifying the efficacy of antidepressant drugs which inhibit the cellular uptake of monoamine neurotransmitters, comprising
    obtaining a buffer-free serum sample from an individual undergoing treatment with one or more antidepressant drug;
    obtaining a cell culture expressing a human monoamine neurotransmitter transporter;
    maintaining the cell culture within the buffer-free drug-containing serum;
    introducing a labeled dose of monoamine neurotransmitter to the drug-containing serum; and
    measuring the uptake of labeled neurotransmitter into cells of the culture, wherein the uptake of labeled neurotransmitter is utilized to determine the effectiveness of the monoamine neurotransmitter reuptake inhibition of the antidepressant drug treatment of the individual.

2. The assay method of claim 1, further comprising the step of
    comparing the uptake of the labeled neurotransmitter with a baseline uptake value for the individual in the absence of antidepressant drug, thereby determining the percentage of neurotransmitter inhibition due to the drug dosage present within the drug-containing serum sample.

3. The assay method of claim 1, further comprising the step of repeating the method for serum samples containing varying dosages of antidepressant drug in order to determine the most efficacious dose for the individual.

4. The assay method of claim 1, wherein the one or more antidepressant drug is one or more compositions that inhibit the transport of monoamine neurotransmitters.

5. The assay method of claim 1, wherein the monoamine neurotransmitters are selected from serotonin, norepinephrine, dopamine, and combinations thereof.

6. The assay method of claim 1, wherein the antidepressant drugs are selected from the group consisting of noradrenergic reuptake inhibitors, 5-HT reuptake inhibitors, dopamine reuptake inhibitors, and combinations thereof.

7. The assay method of claim 1, wherein no more than 2% (v/v) of buffer is introduced to the drug-containing serum at any time during the assay.

8. An assay method for identifying the efficacy of antidepressant drugs which inhibit the cellular uptake of monoamine neurotransmitters, comprising obtaining a buffer-free serum sample from an individual undergoing treatment with one or more monoamine neurotransmitter reuptake inhibitor;
    obtaining a cell culture expressing a human monoamine neurotransmitter transporter;
    maintaining the cell culture within the buffer-free inhibitor-containing serum;
    introducing a labeled dose of monoamine neurotransmitter to the drug-containing serum; and
    monitoring the uptake of labeled neurotransmitter into cells of the culture, wherein the uptake of labeled neurotransmitter is utilized to determine the effectiveness of the monoamine neurotransmitter reuptake inhibition of the antidepressant drug treatment of the individual.

9. The assay method of claim 8, wherein the monoamine neurotransmitter reuptake inhibitor is selected from the group consisting of paroxetine and desipramine.

10. An assay method for identifying the efficacy of antidepressant drugs which inhibit the cellular uptake of monoamine neurotransmitters, comprising the step of
    measuring the uptake of labeled monoamine neurotransmitter into cells of a culture while maintaining the culture in a buffer-free serum sample.

11. The assay method of claim 10, wherein the cells of the culture express a human monoamine neurotransmitter transporter.

* * * * *